(12) United States Patent
Fadler et al.

(10) Patent No.: US 6,986,603 B2
(45) Date of Patent: Jan. 17, 2006

(54) ABOVE-TABLE TRANSILLUMINATION DEVICE WITH SWIVEL-LOCKABLE X-RAY RADIATOR

(75) Inventors: Franz Fadler, Hetzles (DE); Peter Knappe, Bamberg (DE); Stefan Leidenberger, Effeltrich (DE)

(73) Assignee: Siemens Aktiengesellschaft, Munich (DE)

( * ) Notice: Subject to any disclaimer, the term of this patent is extended or adjusted under 35 U.S.C. 154(b) by 729 days.

(21) Appl. No.: 10/086,386

(22) Filed: Mar. 1, 2002

(65) Prior Publication Data

US 2002/0136355 A1 Sep. 26, 2002

(30) Foreign Application Priority Data

Mar. 26, 2001 (DE) .......................... 201 05 190 U

(51) Int. Cl.
*A61B 6/00* (2006.01)

(52) U.S. Cl. ...................................... 378/197; 378/193

(58) Field of Classification Search ................ 378/193, 378/196, 197, 198
See application file for complete search history.

(56) References Cited

U.S. PATENT DOCUMENTS 5,838,764 A 11/1998 Saffer et al.

FOREIGN PATENT DOCUMENTS

| DE | 30 09 496 | 9/1981 |
| DE | OS 41 08 593 | 9/1992 |
| DE | 42 00 654 | 2/1993 |

*Primary Examiner*—Edward J. Glick
*Assistant Examiner*—Chih-Cheng Glen Kao
(74) *Attorney, Agent, or Firm*—Schiff Hardin LLP

(57) ABSTRACT

An above table transillumination device has an X ray radiator that can be rotated around the horizontal axis of the radiator stand and that has a swivel lock having a manually actuatable unlocking lever. The unlocking lever is arranged at the front side of the radiator carrier facing away from the radiator stand and is connected to the lever of the swivel lock via a transmission device.

3 Claims, 4 Drawing Sheets

ABOVE-TABLE TRANSILLUMINATION DEVICE WITH SWIVEL-LOCKABLE X-RAY RADIATOR

BACKGROUND OF THE INVENTION

1. Field of the Invention

The present invention is directed to an above-table transillumination device of the type having X-ray source that can be rotated around the horizontal axis of the radiator stand and that has a swivel lock with a manually actuatable unlocking lever.

2. Description of the Prior Art

The manually actuatable element for unlocking the radiator rotation at an above-table transillumination device is located, for example, behind the radiator directly at the location of the radiator carrier at which the rotary plane between the radiation carrier and the horizontal arm of the radiator stand is located. The latch lever of the swivel lock, of course, also lies in this plane, so that the manually actuatable unlocking lever thereof can be very easily arranged at this location. The unlocking lever, however, lies at a height of about two meters above the floor and is also at the side of the device away from the operator side of the device, so that it is nearly impossible for an operator of normal stature to reach the unlocking lever with his or her hand.

Additionally, electromagnetic interlocks for the rotatable radiation carrier are known so that user friendly remote unlocking is possible. These arrangements, however, are extremely complicated, expensive and susceptible to malfunction compared to manually actuatable swivel locks.

SUMMARY OF THE INVENTION

An object of the present invention is to provide an above-table transillumination device of the type initially described which allows a simpler and more easily accessible unlocking of the radiator rotation.

This object, is inventively archived in a transillumination device wherein the unlocking lever for the radiator is arranged at front side of the radiator carrier that faces away from the radiator stand and is connected to the latch lever of the swivel lock via a transmission device.

Due to the inventive relocation of the unlocking lever, it is still at a height of approximately two meters but close to the front edge of the patient support table at which the operator stands, so that the operator can actuate the unlocking lever significantly better without having to reach across the table toward the back.

The transmission device can thereby be fashioned in a large variety of ways, for example as a toothed rack transmission or gear wheel transmission. Preferably, a Bowden cable can be employed as the transmission device for connecting the unlocking lever to the latch lever of the swivel lock, this being able to be relocated to the inside of the radiation carrier in a very simple way and without impeding the other installed parts of the radiation carrier.

In addition to the possibility of providing a simple unlocking lever fashioned as an L-shaped swivel lever, it has proven especially expedient in an embodiment of the invention for the unlocking lever to be integrated in an essentially C-shaped handle of the radiation carrier.

Instead of attaching the unlocking lever so as to be simply easily accessible as a separate lever at the C shaped handle of the radiation carrier, according to a further feature of the invention, the handle of the radiation carrier is pivotable around the axis of its fastening leg, and is also directly fashioned as the unlocking lever. In order to initiate a turning of the radiator, the manual lever is first swiveled somewhat downwardly, causing the latch lever of the swivel lock to be released via the Bowden cable, and subsequently the rotation of the radiator can ensue by swiveling the handle that has been turned downwardly in this way.

DESCRIPTION OF THE PREFERRED EMBODIMENTS

Figure 1:
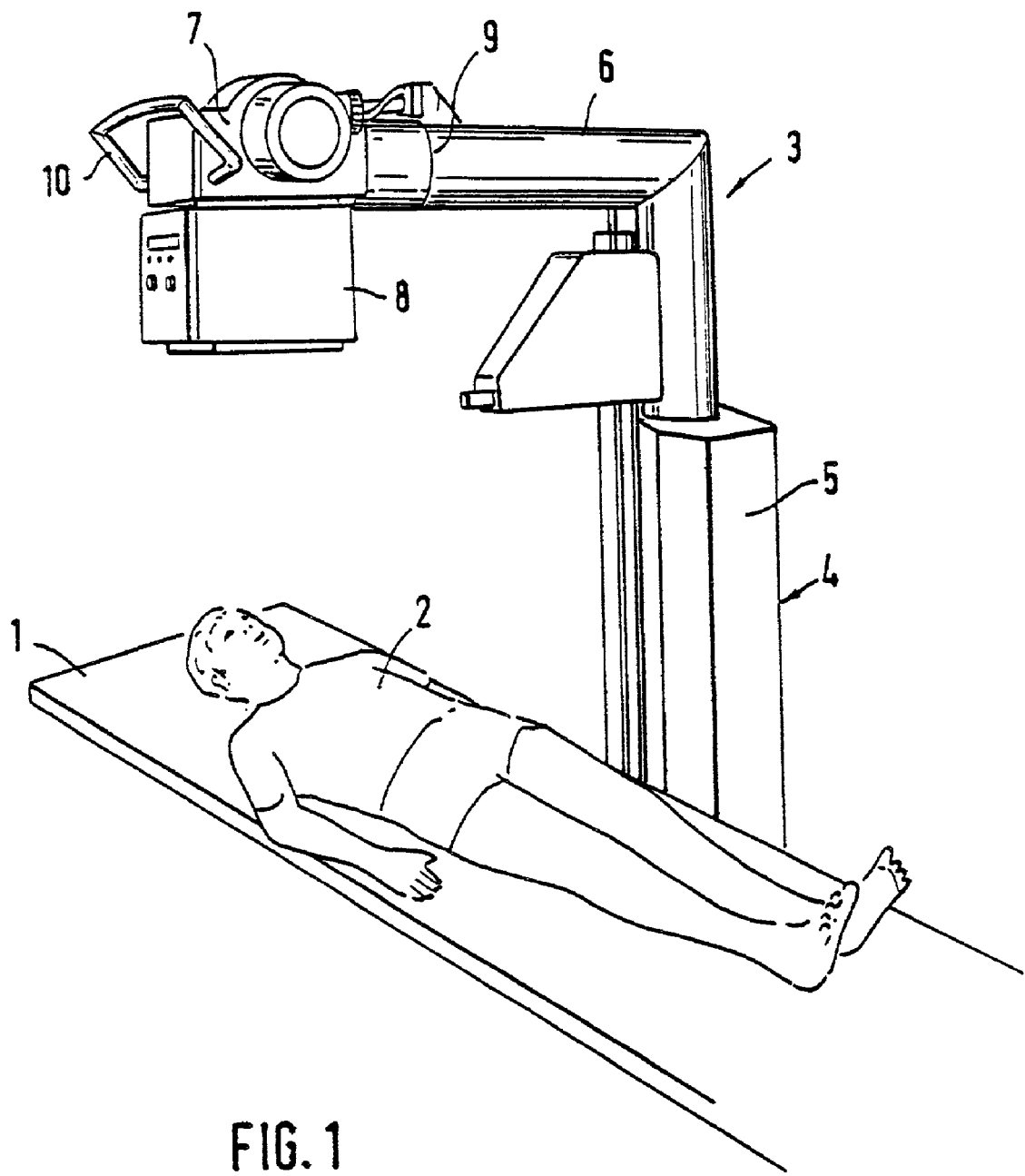
FIG. 1 is a schematic, perspective view of an inventive above-table transillumination device.
Figure 2:
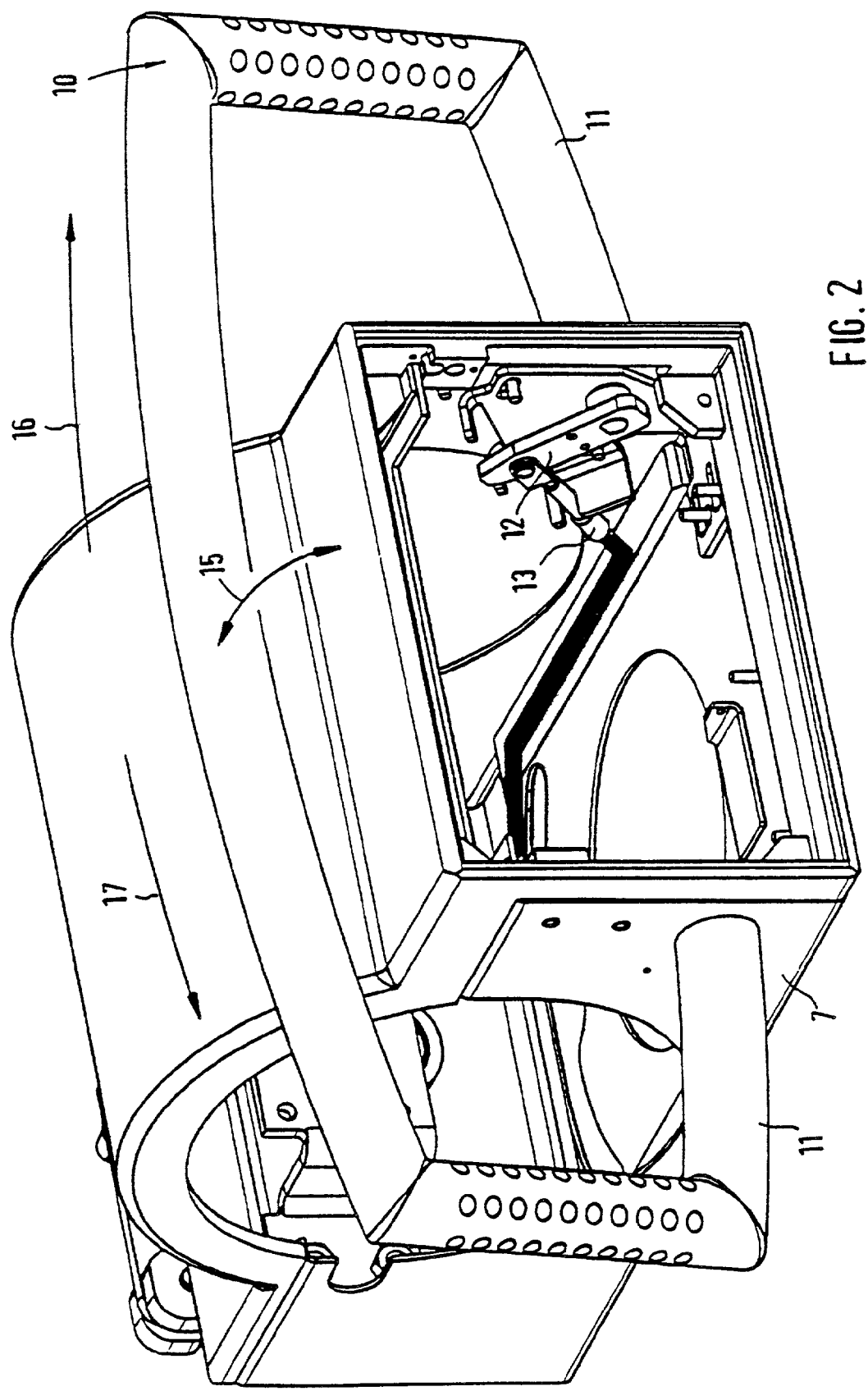
FIG. 2 is an enlarged perspective view of the opened inventive radiator carrier as seen obliquely toward the front.
Figure 3:
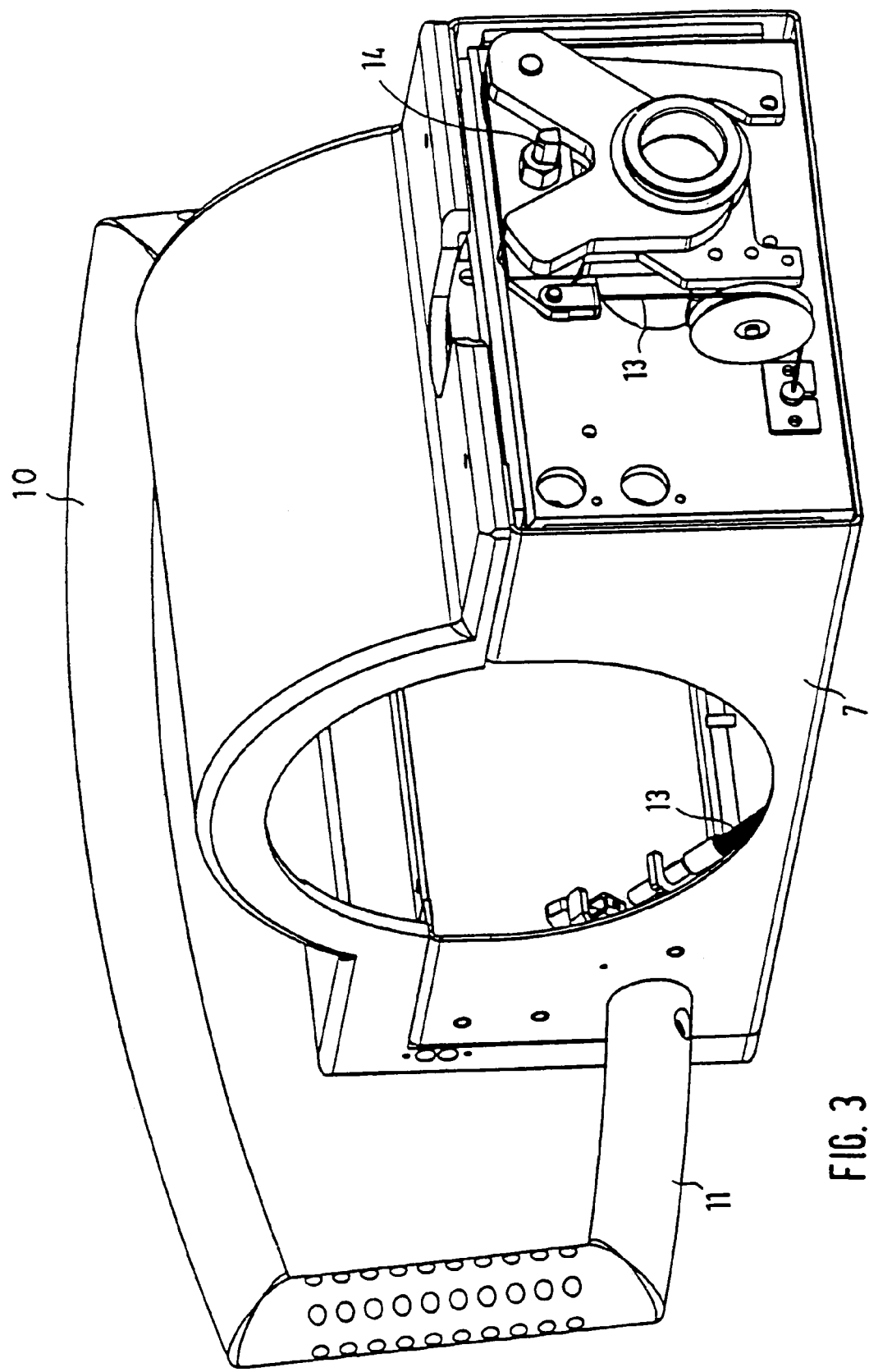
FIG. 3 is a partially opened view of the radiator carrier of FIG. 2 as seen obliquely from behind.

FIG. 1 schematically shows a patient 2 lying on an adjustable patient support table 1 under an above table transillumination device 3 having an essentially L shaped radiator stand 4 with a radiator support column 5 and an essentially horizontal carrier arm 6 at which the radiator carrier 7 for the actual radiator 8 is pivotably seated. The swiveling plane thereby lies approximately in the plane behind the radiator carrier 7, so that the unlocking lever previously arranged at this location was very difficult to reach for the operator standing in front of the patient table 1, the operator usually being located at that side of the radiator stand distant from the column 5. Inventively, in the arrangement according to FIGS. 1 through 3 that the essentially C shaped manual handle 10, with which the swiveling of the radiator 3 is to ensue, is also simultaneously fashioned as the unlocking lever. This is accomplished by the two fastening legs 11 of the manual handle 10 being pivotably seated at the radiator housing 7. A lever arm 12 is secured to the end of one of the fastening legs 11, this lever arm 12 being connected via a Bowden cable 13 to the latch lever 14 that, lying at the backside of the radiator carrier 7 in the swiveling plane 9, can engage into a locking template (not shown) having a number of incisions for setting different swiveled radiator positions. For swivel unlocking, the manual handle 10 is first swiveled down in the direction of the double arrow 15, causing the latch lever 14 to be actuated via the lever 12 and the Bowden cable 13 and is moved out of its locked position. Subsequently, a swivel of the handle 10 in the direction of the arrow 16 or of the arrow 17 can ensue by turning the wrist of the user, and thus the desired rotated radiator position can be set. As soon as the desired position has been found, the manual handle 10 is moved back in the direction opposite the previous unlocking swivel, and the latch lever 14 engages in the closest latch position of the lock template. A spring can also be provided in the Bowden cable 13 that, when the manual handle 10 is swiveled upwardly, pre stresses the latch lever 14 in the locked position, so that it engages into the next latch incision.

Figure 4:
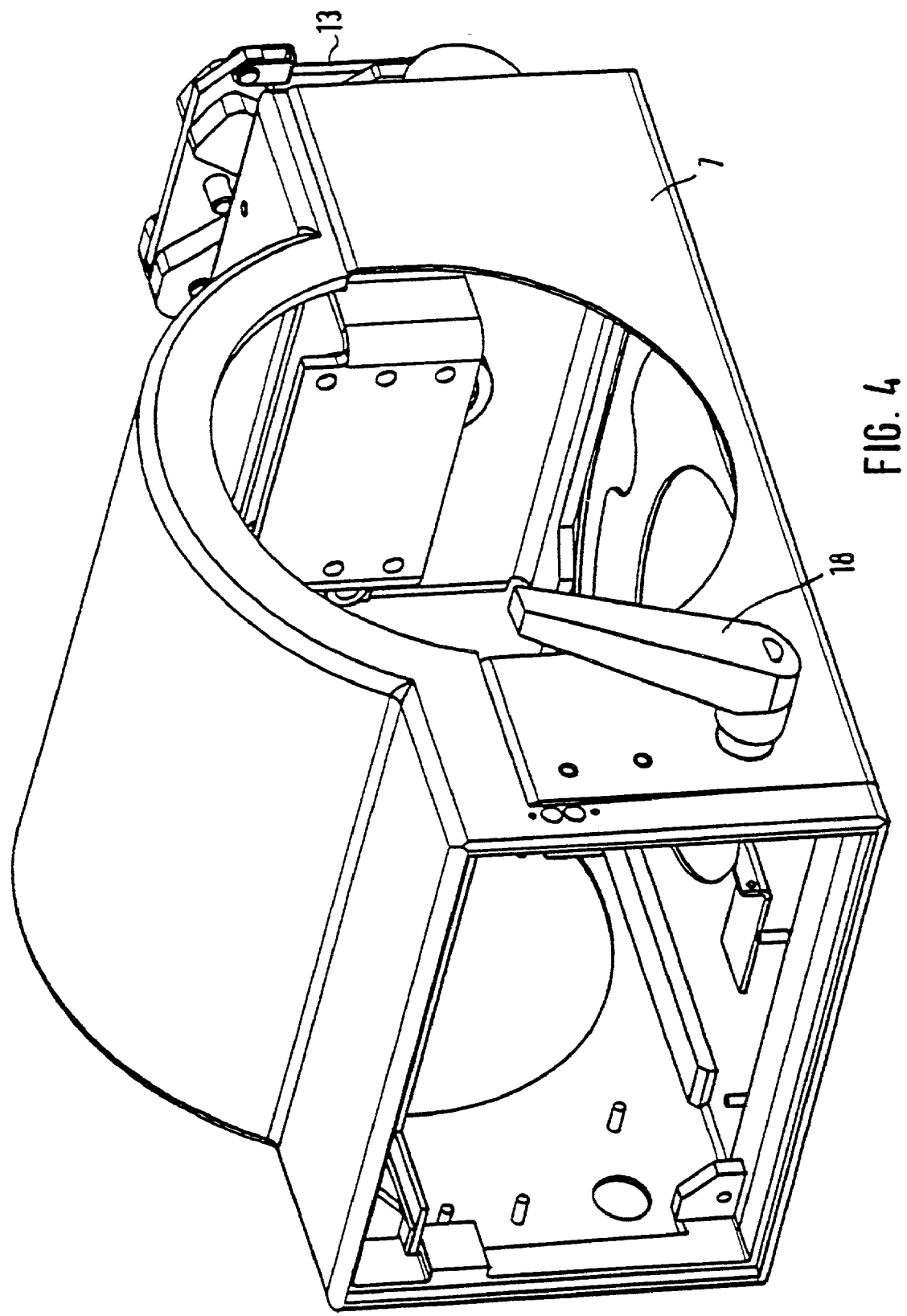
FIG. 4 is a perspective front view of an opened, simplified inventive radiator carrier having a simple unlocking lever, in a view corresponding to FIG. 2.

FIG. 4 shows a simplified embodiment wherein a manual handle 10 serving the purpose of swiveling the radiator carrier 7 with the radiator 8 is omitted. Here, the swivel ensues by direct grasping of the housing of the radiator carrier or of the radiator with one leg, and the unlocking lever 18 is fashioned as a simple lever. A transmission lever connected to the Bowden cable 13 is again seated on the axis of the unlocking lever 18, corresponding to the lever 12 in the exemplary embodiment according to FIGS. 1 through 3.

Although modifications and changes may be suggested by those skilled in the art, it is in the intention of the inventors to embody within the patent warranted hereon all changes and modifications as reasonably and properly come within the scope of their contribution to the art.

We claim:

1. An above table transillumination device comprising:
   a radiator stand having a horizontal axis;
   an x ray radiator;
   a radiator carrier to which said x ray radiator is mounted, said radiator carrier being rotatable around said horizontal axis for simultaneously rotating said x-ray radiator;
   an anti rotation lock disposed for interacting between said radiator carrier and said radiator stand to, in a locked state, prevent said rotation of said radiator carrier around said horizontal axis, said lock having a release lever which, when released, allows said rotation; and
   said radiator carrier having a handle forming a manually actuatable unlocking lever disposed at a front side of said radiator carrier facing away from said radiator stand, and a transmission device connecting said manually actuatable unlocking lever to said release lever of said lock allowing unlocking of said lock by manual actuation of said unlocking lever, said handle being fastened to said radiator carrier by fastening legs around which said handle is pivotable relative to said radiator carrier, with pivoting of said handle releasing said release lever of said lock.

2. An above table transillumination device as claimed in claim 1 wherein said transmission device is a Bowden cable.

3. An above table transillumination device as claimed in claim 1 wherein said handle is C shaped.

* * * * *